United States Patent
Sabczynski et al.

(10) Patent No.: US 9,993,663 B2
(45) Date of Patent: Jun. 12, 2018

(54) ESTIMATING POSITION OF AN ORGAN WITH A BIOMECHANICAL MODEL

(71) Applicant: KONINKLIJKE PHILIPS N.V., Eindhoven (NL)

(72) Inventors: Jörg Sabczynski, Norderstedt (DE); Bharat Ramachandran, Morganville, NJ (US); Ehsan Dehghan Marvast, New York, NY (US); Weihua Zhou, Atlanta, GA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 165 days.

(21) Appl. No.: 15/027,317

(22) PCT Filed: Oct. 9, 2014

(86) PCT No.: PCT/EP2014/071599
§ 371 (c)(1),
(2) Date: Apr. 5, 2016

(87) PCT Pub. No.: WO2015/055485
PCT Pub. Date: Apr. 23, 2015

(65) Prior Publication Data
US 2016/0236009 A1    Aug. 18, 2016

Related U.S. Application Data

(60) Provisional application No. 61/891,521, filed on Oct. 16, 2013.

(30) Foreign Application Priority Data

Nov. 14, 2013  (EP) ..................................... 13192870

(51) Int. Cl.
*G06K 9/00*       (2006.01)
*A61N 5/10*       (2006.01)
(Continued)

(52) U.S. Cl.
CPC ............ *A61N 5/1037* (2013.01); *A61B 5/103* (2013.01); *A61B 5/113* (2013.01); *A61N 5/10* (2013.01);
(Continued)

(58) Field of Classification Search
None
See application file for complete search history.

(56) References Cited

U.S. PATENT DOCUMENTS

2004/0254773 A1   12/2004  Zhang
2009/0175406 A1    7/2009  Zhang
(Continued)

FOREIGN PATENT DOCUMENTS

WO       2012/168869       12/2012

OTHER PUBLICATIONS

Anne-Laure Didier (A chest wall model based on rib kinematics, IEEE, 2009, pp. 159-164).*

(Continued)

*Primary Examiner* — Weiwen Yang

(57) ABSTRACT

There is presented a method 100 and apparatus 200 to measure the surface of the patient (thorax and abdominal regions), e.g., during therapy delivery and (if necessary) while imaging. Together with biomechanical considerations the position of internal structures of the patient, such as an organ, and optionally a tumor in an organ, is inferred from the measured patient surface. In case the patient breaths and thus the organ and/or tumor moves, the position may be determined, which may be advantageous during, e.g., radiation therapy, since it enables that whenever the tumor is at the right position according to the radiation therapy plan, the radiation is switched on. In a specific embodiment, a finite element model is employed.

20 Claims, 6 Drawing Sheets

(51) Int. Cl.
*A61B 5/103* (2006.01)
*A61B 5/113* (2006.01)
*A61B 6/03* (2006.01)
*A61B 5/055* (2006.01)

(52) U.S. Cl.
CPC ......... *A61N 5/1049* (2013.01); *A61N 5/1067* (2013.01); *A61N 5/1077* (2013.01); *A61B 5/055* (2013.01); *A61B 6/032* (2013.01); *A61N 2005/1057* (2013.01); *A61N 2005/1059* (2013.01)

(56) References Cited

U.S. PATENT DOCUMENTS

| | | |
|---|---|---|
| 2010/0198101 A1 | 8/2010 | Song |
| 2011/0081002 A1 | 4/2011 | Keall |
| 2012/0106704 A1 | 5/2012 | Maurer |
| 2012/0109608 A1 | 5/2012 | Core |
| 2013/0023715 A1* | 1/2013 | Raleigh ............... A61N 5/1037 600/1 |
| 2013/0165770 A1 | 6/2013 | Li |

OTHER PUBLICATIONS

Allsop, et al., "Respiratory function monitoring using a real-time three-dimensional fiber-optic shaping sensing scheme based upon fiber Bragg gratings", J Biomed Opt. Nov. 2012; 17(11).

Hostettler, et al., "Real Time Simulation of Organ Motions Induced by Breathing: First Evaluation on Patient Data" In: "Field Programmable Logic and Application", Jun. 10, 2006.

Hostettler A et al: "A real-time predictive simulation of abdominal viscera positions during quiet free breathing", Progress in Biophysics and Molecular Biology, Pergamon Press, Oxford, GB, vol. 103, No. 2-3, Dec. 1, 2010.

Alexandre Hostettler et al: "Bulk modulus and volume variation measurement of the liver and the kidneys in vivo using abdominal kinetics during free breathing", Computer Methods and Programs in Biomedicine, vol. 100, No. 2, Nov. 1, 2010.

J.R. McClelland et al: "Respiratory motion models: A review", Medical Image Analysis, vol. 17, No. 1, Jan. 1, 2013 (Jan. 1, 2013), pp. 19-42, XP055106223.

Schweikard A et al: "Fiducial-less respiration tracking in radiosurgery", Lecture Notes in Computer Science/Computational Science > (EUROCRYPT )CHES 2008, Springer, DE, vol. 3217, Jan. 1, 2004 (Jan. 1, 2004), pp. 992-999, XP009086135.

* cited by examiner

US 9,993,663 B2

ESTIMATING POSITION OF AN ORGAN WITH A BIOMECHANICAL MODEL

CROSS REFERENCE TO RELATED APPLICATIONS

This application is the U.S. National Phase application under 35 U.S.C. § 371 of International Application No. PCT/EP2014/071599, filed Oct. 9, 2014, published as WO 2015/055485 on Apr. 23, 2015, which claims the benefit of European Patent Application Number 13192870.7 filed Nov. 14, 2013 and U.S. Provisional patent Application No. 61/891,521 filed Oct. 16, 2013. These applications are hereby incorporated by reference herein.

FIELD OF THE INVENTION

The present invention relates to the field of determining a position of an organ in a patient, more particularly the present invention relates to a method, an apparatus and a computer program for determining an organ which may move and/or change shape due to breathing.

BACKGROUND OF THE INVENTION

Determination of a position of an organ within a patient may be relevant for various reasons, such as for enabling targeting delivery of radiation to treat pathological anatomies such as tumors or lesions within the organ. This may in particular be relevant for organs which may move and/or change shape due to breathing.

In the reference US 2009/0175406 A1 a method and apparatus for tracking a pathological anatomy within a patient's body is described. A data model of a skin surface of the patient's body may be acquired using light reflected from the skin surface. The data model can be matched with skin surfaces reconstructed and/or interpolated from four-dimensional (4D) diagnostic imaging data, such as 4D CT data, to determine a temporal phase of the patient's respiratory motion. The identified temporal phase may then be used in conjunction with the diagnostic imaging data to identify a location of the pathological anatomy within the patient's body.

SUMMARY OF THE INVENTION

It would be advantageous to provide a method for estimating organ coordinates indicative of a position and shape of at least a part of an organ which may move and/or change shape due to breathing, which can be carried out faster, cheaper, more precise and/or which is more convenient to the patient.

In a first aspect, the invention provides a method for estimating, such as estimating at a second point in time, organ coordinates, such as coordinates indicative of a position and/or shape, of at least a part of an organ which may move and/or change shape due to breathing in an associated patient, the method comprising:

obtaining a biomechanical model of said associated patient, said biomechanical model being based on three-dimensional data indicative of only internal structures of the thorax of said associated patient at a first point in time, obtaining surface coordinates indicative of a position and shape at a second point in time of at least a part of the surface of the thorax of said associated patient, and at least a part of the surface of the abdomen of said associated patient so as to enable estimating an external abdominal volume, obtaining the organ coordinates, such as obtaining the organ coordinates at a second point in time, such as obtaining the organ coordinates corresponding to a second point in time, by inputting said surface coordinates in said biomechanical model, and outputting from said biomechanical model the organ coordinates, wherein said biomechanical model models at least a part of an internal abdominal volume, such as a significant part of an internal abdominal volume, such as a part of the internal abdominal volume corresponding to abdominal tissue, such as an internal abdominal volume, and tissue of the chest wall of said patient, as substantially incompressible, such as incompressible.

It is noted that the steps of the method may not necessarily have to be carried out successively. However, in a specific embodiment, the method steps are carried out sequentially as listed.

By 'organ coordinates of at least a part of an organ' may be understood coordinates which may enable determining the position of the organ with respect to the surface of the patient and/or a fixed coordinate system, for example a laboratory coordinate system, and/or coordinates furthermore provide information on the shape of the organ, such as information which enable determining a position of a structure within the organ. Thus, said organ coordinates may be understood to be organ coordinates indicative of a position and shape of at least a part of an organ.

By 'organ' may be understood an organ as is generally known in the art, which may for example be a lung, a liver or a spine.

By 'an associated patient' may be understood a patient which is not part of the claimed invention. It is understood that 'patient' and 'associated patient' is used interchangeably throughout the present description.

By 'biomechanical model' may be understood one or more mathematical equations which relate displacement at one point in a system/patient with displacement at another point in the system/patient. In particular embodiments, the biomechanical model may be a finite element model.

By 'biomechanical model of said associated patient' may be understood a biomechanical model enabling estimating changes, such as changes in volume or forces or displacements, at one point with estimated changes at another point. For example, if it is known from measurements that the external abdominal volume has increased or decreased, such as increased or decreased relative to some reference state, then it may be possible to utilize at least this information to estimate the organ coordinates. It may be understood that the 'biomechanical model of said associated patient' comprises relevant structures of the associated patient, such as information relating to three-dimensional data indicative of internal structures of the thorax of said associated patient at a first point in time, and surface coordinates indicative of a position and shape at a first point in time of at least a part of the surface of the thorax of said associated patient, and at least a part of the surface of the abdomen of said associated patient so as to enable estimating an external abdominal volume.

It may be understood that in an embodiment, the 'biomechanical model of said associated patient' may be based on three-dimensional data indicative of a position and shape of at least a part of the organ of said associated patient, such as structures of interest, such as the lung, the diaphragm, and/or a tumor of said associated patient, at a first point in time, and surface coordinates indicative of a position and shape at a first point in time of at least a part of the surface of the thorax of said associated patient, and at least a part of the surface of the abdomen of said associated patient so as to enable estimating an external abdominal volume.

By 'three-dimensional data of at least a part of the organ of said associated patient' may be understood three-dimensional (3D) data which is indicative of internal structures, such as data which is indicative of a shape and/or position of internal structures, such as one or more organs, such as the organ, within said patient. It may be understood that these data may also be indicative of surface coordinates corresponding to the position and shape of at least a part of the organ. It may be understood that the three-dimensional data are indicative of internal structures at at least one point in time, such as at one point in time, such as at one previous point in time, such as at the first point in time. It may be understood that said three-dimensional data links the position and/or shape of one or more internal structures, such as a position and shape of at least a part of the organ, with surface coordinates at at least one point in time, such as the first point in time. It may be understood that the three-dimensional data may also be indicative of surface coordinates, such as surface coordinates being relative to the position of at least a part of the organ, such as surface coordinates being indicative of a position and shape at a first point in time of at least a part of the surface of the thorax of said associated patient, and/or at least a part of the surface of the abdomen of said associated patient, such as surface coordinates enabling estimating an external abdominal volume.

It may be understood that the spatial configuration of the associated patient, such as the breathing state, such as the point in a breathing cycle, may be a particular configuration at the at least one point in time. Said 3D data may in exemplary embodiments have been obtained by CT scanning, ultrasound and/or NMR imaging and/or via a surface determining unit for obtaining surface coordinates indicative of a position and shape of at least a part of the surface of the thorax of said associated patient and/or at least a part of the surface of the abdomen of said associated patient, such as enabling estimating an external abdominal volume.

By 'first point in time' may be understood a point in time, which may be in the past, such as data being obtained at a first point in time or representative of an associated patient at a first point in time may have been previously obtained. It may also be understood that the first point in time, may correspond to a certain breathing status, such as a certain point in a breathing cycle, and that the data corresponding to the first point in time may be gathered for a plurality of first points in time, which span a first period of time, such as would be the case for gated imaging.

By 'second point in time' may be understood a point in time, which may be in the past or present, such as said data having been previously obtained or may be obtained in the present. It may be understood that the first point in time and the second point in time may be different points in time, such as the second point in time occurring a finite time after the first point in time. It may furthermore be understood, that the breathing status, such as the configuration of lungs and abdomen may be different at the first point in time compared to the second point in time.

By 'surface coordinates indicative of a position and shape' may be understood data which is provided in a three-dimensional coordinate system, but which is representative of a position and shape of a surface, such as a surface of a patient, such as an outer surface of a patient, such as a skin surface of a patient.

By 'the surface of the thorax of said associated patient' may be understood an outer surface of the thorax, such as a skin surface of the thorax, where thorax is understood as is common in the art.

By 'the surface of the abdomen of said associated patient' may be understood may be understood an outer surface of the abdomen, such as a skin surface of the abdomen, where abdomen is understood as is common in the art.

By 'external abdominal volume' may be understood the volume of the abdomen as measured from the outside, such as an outer volume of the abdomen or the abdominal region, such as a volume of the abdomen being bounded towards the outside of the body by the skin surface. In a specific embodiment, the external abdominal volume may be described as a volume enclosed by the surface of the skin of the abdomen. It may be understood that this volume may not necessarily encompass all of the internal structures of the abdomen. It may be understood that it is not necessarily required that the absolute value of the external abdominal volume is measured, since it may be sufficient to know the changes relative to some reference state only.

In a particular embodiment, the 'external abdominal value' is understood to be measured in changes relative to some reference state. A possible advantage of this may be that it makes the calculation simpler and/or that it is not necessary to exactly define where the border of the abdomen is.

By 'so as to enable estimating an external abdominal volume' may be understood that the surface data of the abdomen may enable estimating the external abdominal volume.

By 'outputting from said biomechanical model the organ coordinates' may be understood that the biomechanical model outputs the organ coordinates, such as enables that an external device may access or receive, such as access or receive, the organ coordinates. It may be understood that the organ coordinates output from the biomechanical model, may be indicative of organ coordinates at the second point in time. This may be due to the fact that the surface coordinates input to the biomechanical model corresponds to the second point in time.

By 'internal abdominal volume' may be understood a volume corresponding to the volume of the air, liquids and tissue of the abdomen. As such, the 'internal abdominal volume' may be seen as a 'true volume of the abdomen'. It is noted that it may be seen as an insight of the present inventors that the 'internal abdominal volume' may be modeled as substantially incompressible, such as incompressible. Although gaseous phases may be present the volume of such phases and any pressure difference is small enough that the abdominal tissue nevertheless behaves and may be modeled as substantially incompressible, such as incompressible. In an embodiment, at least a part of the internal abdominal volume is modeled as incompressible, such as the embodiment comprising estimating an amount of gas, such as air, in the abdomen, e.g. from 3D CT images, and taking the compressibility of the gas into account, such as modeling gas as compressible and the remaining parts of the abdomen, such as abdominal tissue, as incompressible. In an embodiment, a significant portion of the 'internal abdominal volume' is modeled as incompressible, such as the 'internal abdominal volume' being modeled as incompressible. It may be understood that it is not necessarily required that the absolute value of the internal abdominal volume is measured, since it may be sufficient to know the changes relative to some reference state only.

In a particular embodiment, the 'internal abdominal value' is understood to be measured in changes relative to some reference state. A possible advantage of this may be that it makes the calculation simpler and/or that it is not necessary to exactly define where the border of the abdomen is.

By 'biomechanical model models internal abdominal volume and tissue of the chest wall of said patient as substantially incompressible' may be understood that each of the internal abdominal volume and the chest wall may be represented in the biomechanical model as substantially incompressible material, such as incompressible material.

By 'incompressible' may be understood that the volume does not change even though external forces may be applied. It is to be understood, that the invention may still exhibit the technical effect for small deviations from exactly incompressible, and that such small deviations from exactly incompressible, are still within the scope of the claims, such as the claims also covering 'substantially incompressible', such as the claims also covering embodiments with volume changes within 10%, such as within 9%, such as within 8%, such as within 7%, such as within 6%, such as within 5%, such as within 4%, such as within 2%, such as within 1%, such as within 0.5%, such as within 0.25%, such as within 0.1%. In a specific embodiment, each of the internal abdominal volume, and the tissue of the chest wall of said patient are modeled as incompressible, such as exactly incompressible.

By 'substantially incompressible' may be understood that the volume does not change substantially even though external forces may be applied. It may be understood that minor deviations from 'incompressible' is within the scope of the claims. In an embodiment any one or both of the internal abdominal volume and the chest wall may be represented in the biomechanical model as substantially incompressible, so that the estimated organ coordinates do not vary significantly with respect to a situation where they were represented in the biomechanical model as exactly incompressible.

It is understood that the method does not require physical interaction with a patient's body and/or involvement of a medical practitioner.

The invention is particularly, but not exclusively, advantageous for obtaining for estimating organ coordinates indicative of a position and shape of at least a part of an organ which may move and/or change shape due to breathing in an associated patient, which may for example be beneficial during radiation therapy.

A possible advantage of the invention may be that it enables repeatedly determining the organ coordinates of a patient which is breathing.

A possible advantage of the invention may be that it makes no assumptions on the character of a breathing cycle. A first possible advantage of this may be that the patient may be allowed to breathe freely. A second possible advantage of this may be that the method may be more precise, since it does not introduce errors due to deviations from an assumed breathing cycle. This advantage may be realized by obtaining the three-dimensional data at any given time, such as the first point in time be any time, such as any time in the past, for any given breathing state, and then subsequently at the second point in time obtain surface coordinates which may via the biomechanical model be employed to calculate the configuration at the second point in time, such as shape an position, of the organ at any other given time (corresponding to the time the surface coordinates are obtained). This enables dispensing with the need for obtaining 3D data more than once, and in particular dispenses with the need for obtaining 3D data at the point in time, such as the second point in time, in which the organ coordinates are needed.

This advantage may be seen as based on the insight that an associated patient may not be confined to breathe in a predictable pattern, i.e., even if numerous 3D data are obtained for an apparently complete breathing cycle, a patient may then later breathe in another manner, thus introducing error if this change in breathing is not taken into account. The present invention may thus be seen as not necessarily relying on an assumption regarding breathing pattern.

Another possible advantage may be that the method does not necessitate more than a single set of three-dimensional data indicative of a position and shape of at least a part of an organ of said associated patient, i.e., it is not necessary to provide multiple sets of such 3D data corresponding to different time points during breathing (such as so-called 4D data). An advantage of this may be that the method may be simpler, faster, cheaper and/or may expose the patient to less radiation.

Another possible advantage may be that the method does not necessitate more than a single set of three-dimensional data indicative of a position and shape of at least a part of an organ of said associated patient, and that this set of 3D data may be obtained prior to determining the organ coordinates. In other words, once the 3D scan is obtained, the organ coordinates may be repeatedly obtained afterwards, which may for example be beneficial during radiation therapy.

In another embodiment there is provided a method wherein said biomechanical model employs as constraints,
the internal abdominal volume, such as a significant part of an internal abdominal volume, such as a part of the internal abdominal volume corresponding to abdominal tissue, such as an internal abdominal volume, and
the surface coordinates indicative of a position and shape of at least a part of the surface of the thorax of said associated patient.

By 'constraints' may be understood fixed values from which the biomechanical model may calculate other values.

In another embodiment there is provided a method wherein said biomechanical model is based on only a single set of three-dimensional data indicative of a position and shape of at least a part of an organ of said associated patient. It may be seen as a possible advantage, that the biomechanical model is based on only a single set of said three-dimensional data, since it may be enable a method which may be simpler, faster, cheaper and/or may expose the patient to less radiation.

In another embodiment there is provided a method wherein only the surface coordinates are input to the biomechanical model in the step of obtaining organ coordinates. It may be seen as a possible advantage, that only the surface coordinates are input to the biomechanical model in the step of obtaining organ coordinates, since it may be enable a method which may be simpler, faster, cheaper and/or may expose the patient to less radiation.

In another embodiment there is provided a method said organ is a lung. In another embodiment, said organ may be any organ which may also undergo breathing motion, such as any one organ chosen from the group of organs comprising liver and spine.

In another embodiment there is provided a method further comprising determining a tumor coordinate indicative of a position of a tumor in the organ, wherein the determination is based on the organ coordinates. An advantage of this may be that it enables providing the tumor coordinate, which may in turn be relevant for a number of purposes, including radiation therapy.

In another embodiment there is provided a method wherein the method further comprising repeatedly determining a tumor coordinate indicative of a position of a tumor in the organ, wherein the determination is based on the organ coordinates. An advantage of this may be that it enables providing the tumor coordinate repeatedly, which may in turn be relevant for a number of purposes, including radiation therapy. It may be understood that this embodiment may be realized by repeating the steps of obtaining surface coordinates, obtaining the organ coordinates and determining a tumor coordinate indicative of a position of a tumor in the organ, wherein the determination is based on the organ coordinates.

In another embodiment there is provided a method wherein the biomechanical model comprises data structures representing chest, the organ and abdomen. The data structures may in exemplary embodiments be any one of NURBS surface, subdivision surfaces, polygon meshes. An advantage of this may be that it provides a method which facilitates determining the position of an internal structure in the organ, such as a tumor.

In another embodiment there is provided a method wherein the biomechanical model comprises a patient-specific mesh of chest, the organ and abdomen. By 'patient-specific mesh' may be understood a polygon mesh, such as a mesh which may be applicable for modeling the chest, the organ and abdomen in polygonal modeling.

This embodiment may relate to a displacement-only method to estimate the motion of the organ, such as diaphragm/lung/tumor from a surrogate displacement signal such as motion of the abdomen, umbilicus, etc. A possible advantage of this embodiment may be that if tumor motion caused by breathing can be accurately estimated, during external beam radiation therapy, the dose to the tumor can be increased without increasing the dose to the healthy tissue. Current models for estimating the diaphragm/lung motion may depend on hard-to-measure force or pressure values. A predefined value can be used in the present embodiment model; however it decreases the accuracy of the output.

In a particular embodiment, there is employed Finite-Element based model that relies only on displacement, and hence, obviates the need for force or pressure values. The model may learn the motion pattern of the diaphragm from a set of patient data sets and applies that to new patients.

In a particular embodiment, Finite Element (FE) based models are employed to simulate the motion of the organ, such as the lung. An FE-based model solves the following equation:

$$Ku=f, \quad (1)$$

where u is nodal displacement of lung tissue, f is the nodal external forces applied to the tissue and K is the stiffness matrix calculated using tissue mechanical properties. In order to calculate u, K and f should be known. However, the measured surface coordinates (which may anywhere in the description be referred to interchangeably as "surrogate signals") are always displacements (such as displacement of chest or abdomen). Therefore, it is not possible to directly measure the nodal forces required in (1). In previous work, the force vector f was populated using predefined pressure values that were not patient specific. A predefined pressure value cannot provide high accuracy as it cannot take into account the inter-patient variability.

In an embodiment there is provided a model-based displacement-only FE model to simulate the organ, such as a lung, and optionally tumor motion, from displacement surrogate signals such as motion/volume of the abdomen, motion of the chest. The advantage of this approach is that it obviates the need for incorporating difficult-to-measure forces and pressure values into the equations.

In another embodiment there is provided a method wherein the method is further comprising any one of:
outputting the tumor coordinate, so as to enable an associated device to receive the tumor coordinate,
outputting a signal indicative of whether or not the tumor coordinate is within a pre-determined volume.

By 'an associated device' may be understood a device capable of performing an interaction with the human body, such as a surgical robot or an actuator. In an embodiment, the associated device may be a radiation source, such as source suitable for providing radiation therapy. It may be understood that associated device may also be a device suitable for controlling a device capable of performing an interaction with the human body, such as a radiation source.

By 'a pre-determined volume' may be understood a volume which has previously been determined, which volume may for example correspond to a volume which is fixed relative to an external device, such as a radiation source. In as specific embodiment, the pre-determined volume corresponds to a volume which may be targeted by a radiation source.

A possible advantage of outputting the tumor coordinate, so as to enable an associated device to receive the tumor coordinate, may be that the external device, such as a radiation source may then be operated accordingly, e.g., by adjusting the target volume or by switching on and off the radiation accordingly. A possible advantage of outputting a signal indicative of whether or not the tumor coordinate is within a pre-determined volume, such as within the target volume of a radiation source, may be that it enables switching on and off the radiation accordingly In a second aspect, the invention provides an apparatus for estimating coordinates indicative of a position and shape of at least a part of an organ which may move due to breathing in an associated patient, the apparatus comprising:
a computer-readable medium suitable for comprising a biomechanical model of said associated patient, said biomechanical model being based on three-dimensional data indicative only internal structures of the thorax of said associated patient at a first point in time,
a surface determining unit for obtaining surface coordinates indicative of a position and shape at a second point in time of
  at least a part of the surface of the thorax of said associated patient, and
  at least a part of the surface of the abdomen of said associated patient (330) so as to enable estimating an external abdominal volume,
a processor operatively connected to the computer readable medium and the surface determining unit for obtaining surface coordinates indicative of a position and shape of the surface of said associated patient at the second point in time, the processor being arranged for obtaining the organ coordinates, by receiving said surface coordinates, inputting said surface coordinates in said biomechanical model, and outputting from said biomechanical model the organ coordinates, wherein said biomechanical model models at least a part of an internal abdominal volume, such as a significant part of an internal abdominal volume, such as a part of the internal abdominal volume corresponding to abdominal tissue, such as an internal abdominal volume, and tissue of the chest wall, as substantially incompressible.

By 'surface determining unit for obtaining surface coordinates' may be understood a device capable of providing information regarding the position and shape of at least a part of a surface of the body of a patient.

In another embodiment there is provided an apparatus wherein the surface determining unit for obtaining surface coordinates indicative of a position and shape of the surface of said associated patient, comprises any one of:

a surface scanner, a fiber optic shape sensing (OSS) garment, and/or a plurality of cameras enabling photogrammetry.

By 'a surface scanner' may be understood a device which scans, such as mechanically or optically scans, a surface enables providing information regarding the position and shape of the surface. The surface scanner may be an optical surface scanner, e.g., a laser range scanner. In an embodiment, possible line-of-sight issues may be overcome by any one of attaching the scanner to a movable structure or using more than one scanner.

By 'a fiber optic shape sensing (OSS) garment' may be understood a collection of fibers for optic shape sensing which may be position on a surface of a patient and provide information regarding the position and shape of at least a part of a surface of the body of a patient. An example of OSS garment may be found in the reference "Respiratory function monitoring using a real-time three-dimensional fiberoptic shaping sensing scheme based upon fiber Bragg gratings", Allsop et al., J Biomed Opt. 2012 November; 17(11), which is hereby incorporated by reference in entirety. A possible advantage of OSS garment may be that there are no line-of-sight issues.

In another embodiment there is provided an apparatus further comprising a source of radiation for external beam therapy which is operatively connected to the processor.

By 'a source of radiation for external beam therapy' may be understood any source capable of providing radiation for external beam therapy. The radiation may be X-ray and electron beams, but may also relate to other types of radiation, such as radiation employing heavier particle beams, particularly proton sources. In a particular application, the source is a linear accelerator (LINAC).

In another embodiment there is provided an apparatus wherein the source of radiation for external beam therapy is arranged for functioning dependent on the position of tumor. By 'functioning dependent on the position of tumor' may be understood that the target area of the source of radiation, and/or the power of the radiation emitted may vary in dependence on the position of the tumor. This may be advantageous for ensuring that the tumor—and not the surrounding healthy tissue receives the radiation.

In another embodiment there is provided an apparatus wherein the computer-readable medium comprises the biomechanical model of said associated patient.

In a third aspect, the invention provides a computer program enabling a processor to carry out the method according to the first aspect.

It is appreciated that the same advantages and embodiments of the first aspect apply as well for the second aspect. In general the first and second aspects may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
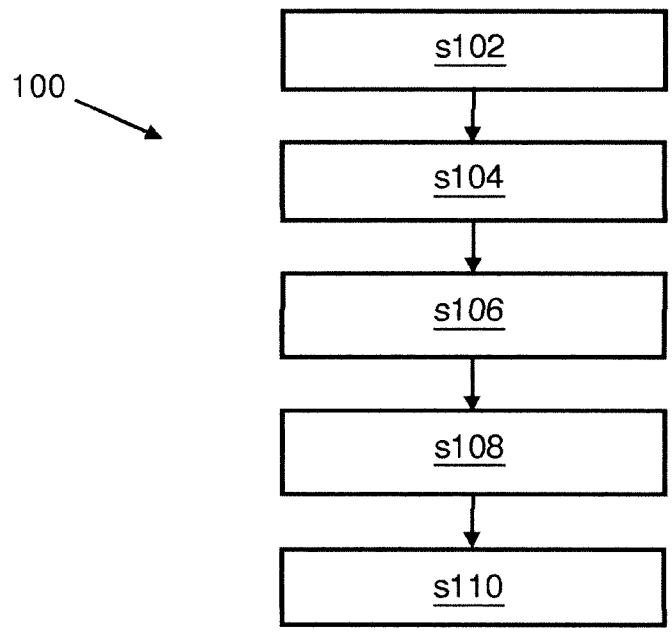
FIG. 1 is a flow chart illustrating a method according to an embodiment of the invention.

FIG. 1 is a flow chart illustrating a method (100) according to an embodiment of the invention for estimating organ coordinates, such as organ coordinates indicative of a position and shape, of at least a part of an organ which may move and/or change shape due to breathing in an associated patient, the method comprising:

obtaining s102 a biomechanical model of said associated patient, said biomechanical model being based on three-dimensional data indicative of only internal structures of the thorax of said associated patient at a first point in time, obtaining s104 surface coordinates indicative of a position and shape at a second point in time of at least a part of the surface of the thorax of said associated patient, and at least a part of the surface of the abdomen of said associated patient so as to enable estimating an external abdominal volume, obtaining s106 the organ coordinates, by inputting said surface coordinates in said biomechanical model, and outputting from said biomechanical model the organ coordinates, wherein said biomechanical model models internal abdominal volume, and tissue of the chest wall of said patient, as substantially incompressible, wherein the method is further comprising determining s108 a tumor coordinate indicative of a position of a tumor in the organ, wherein the determination is based on the organ coordinates, wherein the method further comprising:

outputting s110 the tumor coordinate, so as to enable an associated device to receive the tumor coordinate.

Figure 2:
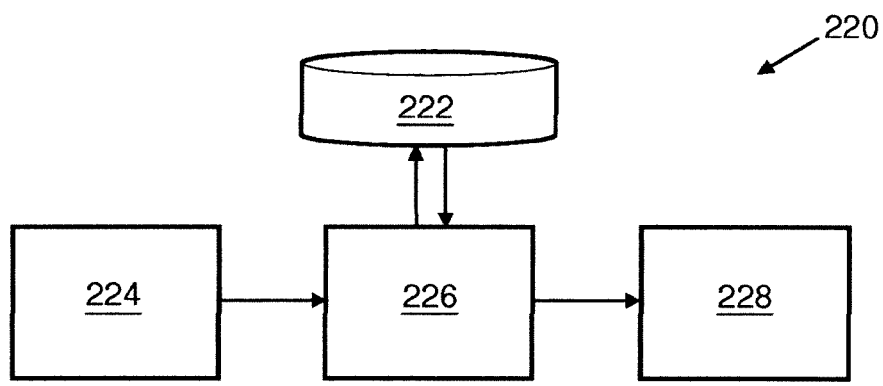
FIG. 2 illustrates an apparatus according to an embodiment of the invention.

FIG. 2 illustrates an apparatus (220) according to an embodiment of the invention for estimating coordinates, such as coordinates indicative of a position and shape, of at least a part of an organ which may move due to breathing in an associated patient (330), the apparatus comprising:

a computer-readable medium (222) suitable for comprising a biomechanical model (352) of said associated patient, said biomechanical model being based on three-dimensional data indicative of only internal structures of the thorax of said associated patient of said associated patient at a first point in time, a surface determining unit (224) for obtaining surface coordinates indicative of a position and shape at a second point in time of
  at least a part of the surface of the thorax (356) of said associated patient, and
  at least a part of the surface of the abdomen (354) of said associated patient, a processor (226) operatively connected to the computer readable medium and the surface determining unit (224) for obtaining surface coordinates indicative of a position and shape of the surface of said associated patient at the second point in time, the processor being arranged for obtaining the organ coordinates, by
  receiving said surface coordinates,
  inputting said surface coordinates in said biomechanical model, and
  outputting from said biomechanical model the organ coordinates, wherein said biomechanical model models abdominal volume, and
  tissue of the chest wall, as incompressible.

Figure 3:
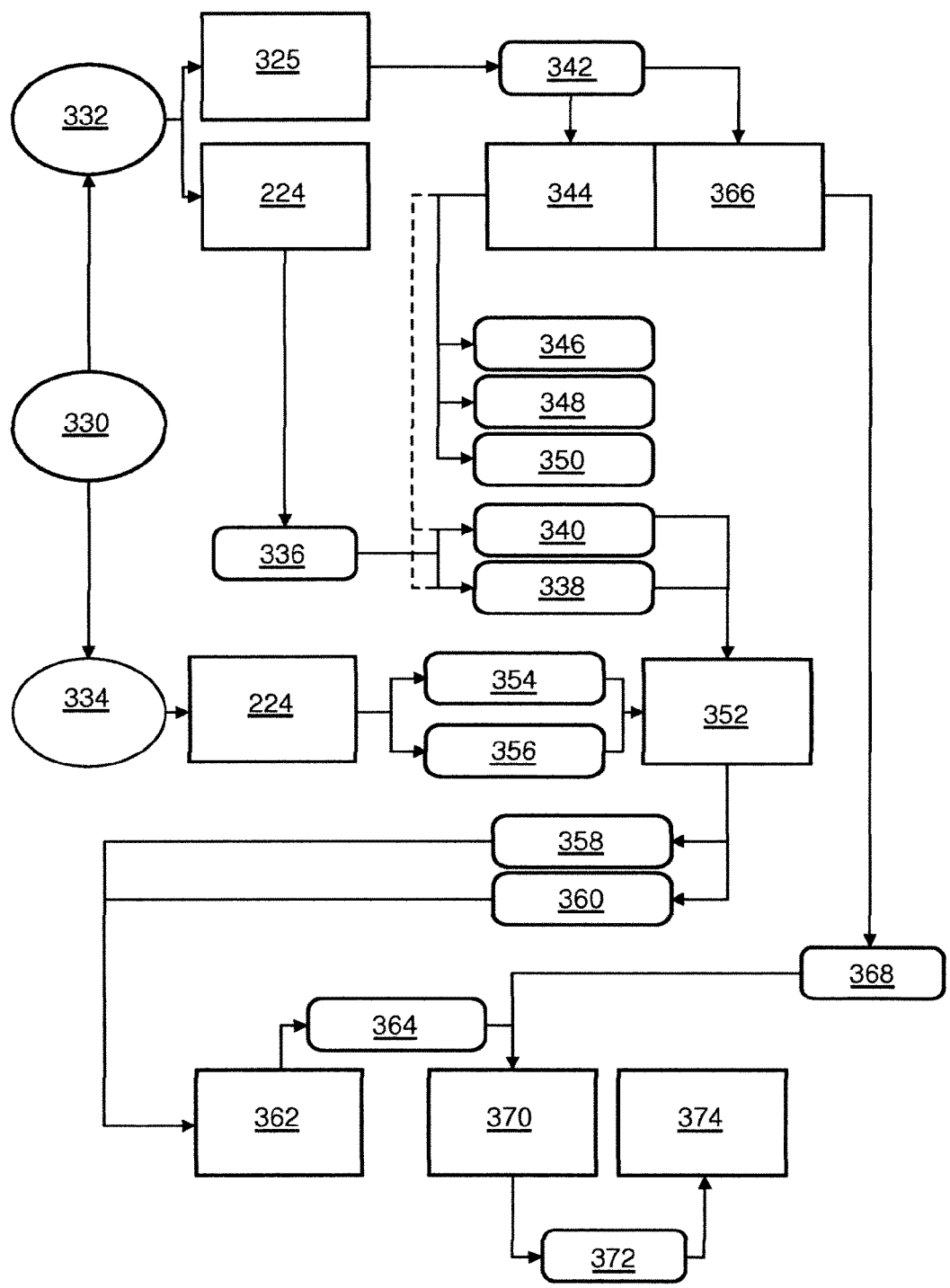
FIG. 3 is a schematic illustrating an embodiment of the invention.

FIG. 3 is a schematic illustrating an embodiment of the invention where the organ is a lung, the figure showing an associated patient 330 which patient may in a first imaging phase 332 (which may correspond to a first point in time) be imaged by a surface determining unit 224 for obtaining surface coordinates 336 corresponding to the configuration of the lung and abdomen during the first imaging phase, such as surface coordinates indicative of a position and shape of at least a part of the surface of the thorax 340 of said associated patient, and at least a part of the surface of the abdomen 338 of said associated patient. The patient may furthermore in the first imaging phase 332 be imaged by an imaging unit 325 for obtaining 3D data 342 indicative of positions of internal structures, which imaging unit may be a CT-scanner or an NMR scanner. The 3D data 342 may be received by an image segmentation unit 344, which may provide information regarding lung surface 346, diaphragm surface 348, and abdomen surface 350 during the first imaging phase. The three-dimensional data may be input to a biomechanical model, such as a biomechanical model 352 of the thorax and the abdomen. It may be understood that the three-dimensional data may include surface coordinates 336 and data from the image segmentation unit 344.

The patient may in a second imaging phase 334 (which may correspond to a second point in time) be imaged by a surface determining unit 224 for obtaining surface coordinates corresponding to the configuration of the lung and abdomen during the second imaging phase, such as surface coordinates indicative of a position and shape of at least a part of the surface of the thorax 356 of said associated patient, and at least a part of the surface of the abdomen 354 of said associated patient. The surface coordinates obtained in the second imaging phase 334 may be input to the biomechanical model 352.

Although the configuration of the lung and abdomen in the first and second imaging phase are not necessarily the same, such as different, such as corresponding to different temporal positions in the breathing cycle, the biomechanical model 352 may provide data 358 corresponding to lung surface and data 360 corresponding to diaphragm surface in the second imaging phase 334.

The data 358 corresponding to lung surface and data 360 corresponding to diaphragm surface in the second imaging phase 334 may be input to a biomechanical model 362 of lung and tumor, which may in turn output a tumor position 364 in the second imaging phase.

In a specific embodiment, the second imaging phase includes radiation therapy. In that embodiment, the 3D data 342 may also be input to a radiation therapy planning workstation 366, which may output a radiation therapy plan 368. The tumor position 364 as well as the radiation therapy plan 368 may be sent to an online control computer 370 for controlling a radiation source 374, such as a linear accelerator. The online control computer 370 may then control the radiation source accordingly, in dependence of the radiation therapy plan 368 and the tumor position 364, such as control whether the radiation source should be 'on' or 'off' 372

In the following the dataflow and workflow an exemplary specific embodiment where the second imaging phase includes radiation therapy for lung cancer radiation therapy is described (see FIG. 3):

Before therapy (cf., the first imaging phase):
1. The thorax of the patient is scanned during a breath hold and a 3D CT scan is created. Structures of interest, such as all structures of interest are covered; for example the lung, the diaphragm, and the tumor.
2. For the biomechanical calculation of the diaphragm position, the knowledge of the shape of the abdomen may be utilized. Due to the X-ray dose associated with CT imaging, it is in general not beneficial to image the abdomen together with the thorax. Therefore, the surface scanner measures the patient's surface during 3D CT imaging. Treatment planning is done based on the 3D CT scan. In an alternative embodiment, which may be advantageous if there is no surface scanner available during CT imaging, the abdomen is imaged together with the thorax using CT imaging.
3. Segmentations of lung, diaphragm, tumor, skin, and other relevant structures are available after treatment planning.
4. External beam radiation therapy is planned based on this 3D CT scan. During therapy (cf., the second imaging phase):
5. For radiation therapy, the patient is positioned in the radiation therapy room and the LINAC is aligned according to the treatment plan.
6. A surface scanner measures the surface of the patient (thorax and abdominal regions).
7. Based on the surface measurement (thorax and abdomen) and the segmentation results (lung and diaphragm), the shape of the thoracic wall, i.e. the outer surface of the lung, is calculated taking into account biomechanical considerations.
8. Based on the outer shape of the lung, the position of the tumor is estimated e.g. with the help of biomechanical models.
9. When the tumor is at the planned position (and the patient position and shape is sufficiently close to the planning), radiation delivery is triggered and the beam is switched on.

Figure 4:
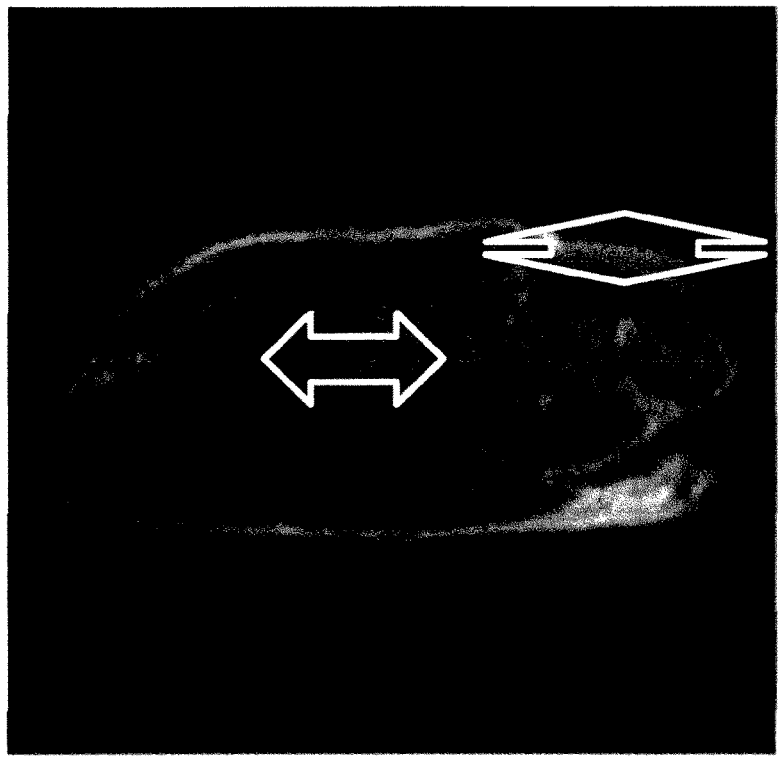
FIGS. 4-5 show diaphragm motion during breathing.
Figure 5:
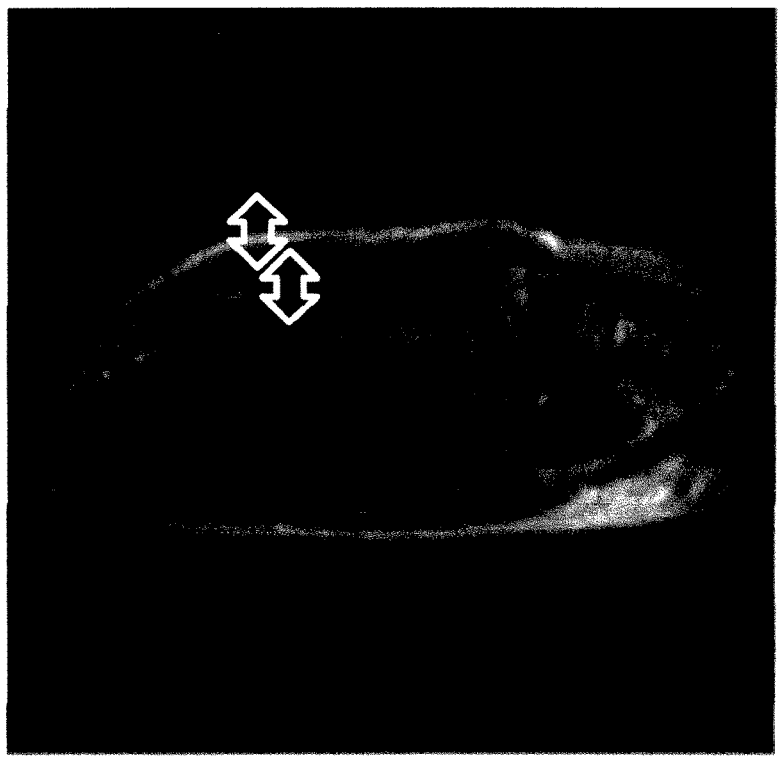

FIGS. 4-5 show diaphragm motion during breathing. It may be seen as a basic insight of the present inventors that the internal abdominal volume, including abdominal tissue, as well as the tissue of the chest wall is almost incompressible. Therefore, any change of the abdominal volume is related to a corresponding change of the diaphragm position, any change in the outer surface of the chest is related to a corresponding change of the lung surface.

FIG. 4 shows that diaphragm motion (as indicated by the left arrow) is highly correlated with external abdominal volume as measured from the outside (as indicated by the right arrow).

FIG. 5 shows that motion of the outside of the chest (as indicated by the upper arrow) is highly correlated with inside motion i.e. lung surface motion (as indicated by the lower arrow).

Figure 6:
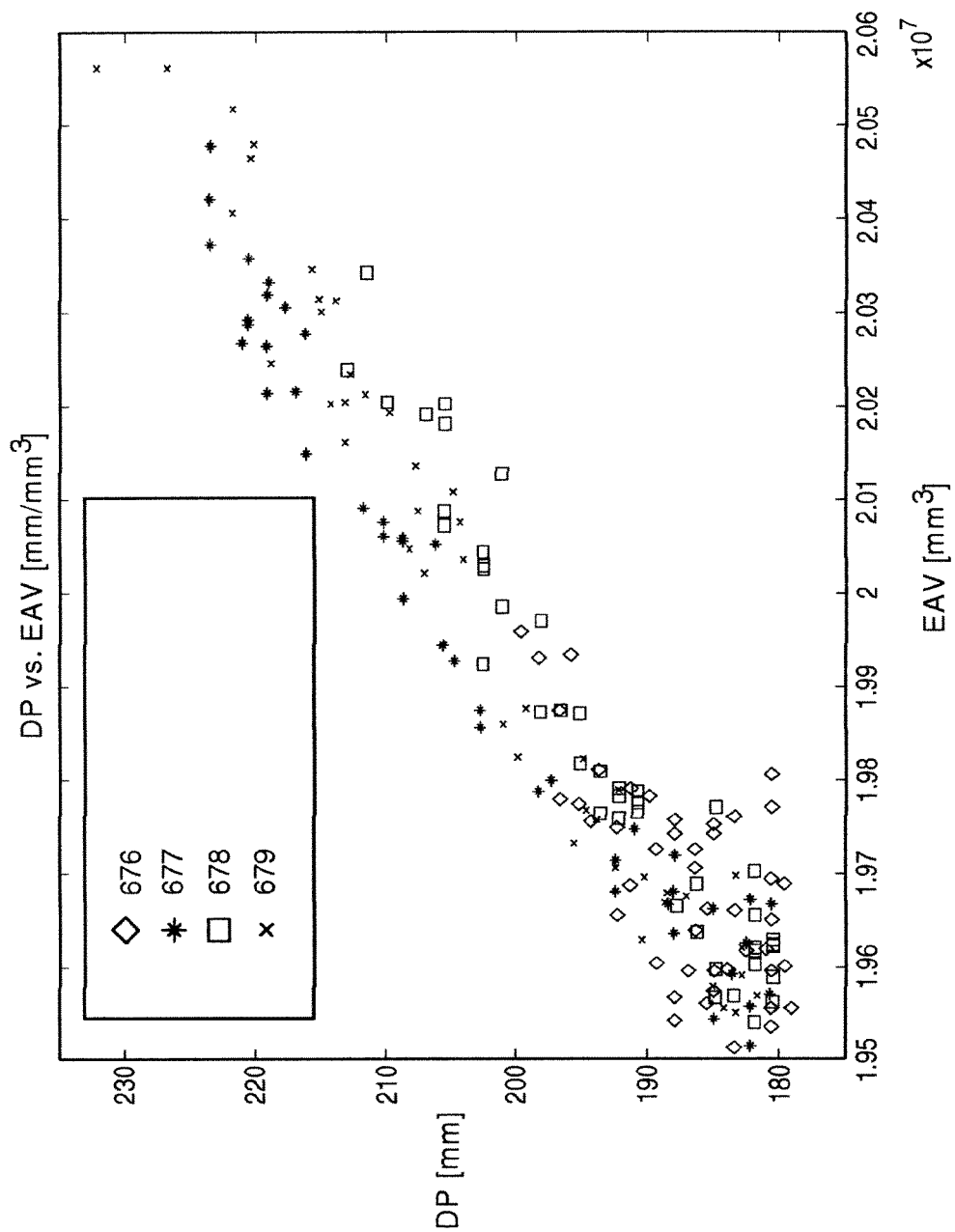
FIG. 6 is a graph showing diaphragm position vs. abdominal volume.

FIG. 6 is a graph showing correlation of diaphragm position and abdominal volume for one of the volunteers from the study. More specifically, the graph shows diaphragm position in head-feet direction vs. external abdominal volume. The horizontal axis shows external abdominal volume (EAV) in cubic millimeters. The vertical axis shows diaphragm position (DP) in millimeters. The data markers represent paradox breathing (676), abdominal breathing (677), thoracal breathing (678) and normal breathing (679). In principle, the gas, which is included in the abdomen e.g. in the stomach or the intestines, is compressible. However, in the one hand the abdominal gas volume is relatively small in relation to the abdominal tissue; on the other hand, pressure changes during breathing are small in the abdomen. Therefore, volume changes of abdominal gas can be neglected as well. Real-time 4D MRI data has been acquired during a volunteer study at Philips Research in Hamburg (Measurement time for a complete volume 0.8 sec). A high correlation of external abdominal volume with diaphragm position has been detected. It is important to note that this correlation is independent of the breathing pattern or depth of breathing. It has been observed for normal, thoracal, abdominal, as well as paradox breathing patterns with deep and flat amplitude (see FIG. 6 for an example from the volunteer study mentioned above).

Diaphragm:

Based on biomechanical considerations, the diaphragm position can be predicted surprisingly well from a measurement of the complete abdominal volume. This has been shown with the help of a volunteer study in which 4D real-time MRI of the thorax and the abdomen was used to assess the breathing motion. The volunteers were asked to breath with flat and deep amplitudes in 4 different breathing patterns: normal, abdominal, thoracal, and paradox breathing. The latter is a yoga exercise with unnatural movements. 3D volumes were recorded every 0.7-0.8 seconds depending on the height of the volunteer. The biomechanically motivated correlation between abdominal volume and diaphragm position was verified for all volunteers, all amplitudes, and all breathing patterns.

Thorax:

The shape of the skin surface of the chest can be measured with the help of the devices such as the surface determining unit for obtaining surface coordinates described elsewhere in the present text. In a first order approximation the thickness of the thorax measured from lung surface to skin is constant. Therefore, it is possible to estimate the lung surface starting from a 3D image of the internal structures of the thorax together with measurements of the outer shape of the patient's thorax.

Together with biomechanical considerations the position of a tumor inside the organ of a patient is inferred from the measured patient surface. This may be relevant, e.g., during therapy delivery, where the patient breathes and thus the tumor moves. Whenever the tumor is at the right position according to the radiation therapy plan, the radiation is switched on.

Lung Surface Estimation

The surface of the organ, such as the lung, is estimated based on the surface coordinates, such as the measurements of the surface scanner. A first order approximation to estimate the lung surface is to assume, that the thickness of the chest wall does not change during breathing. Therefore, the distance of lung surface to outer body surface is constant in the area of the chest. More complex biomechanical models can be used as well. In order to estimate the lower boundary of the lung, the diaphragm, more complex calculations may be carried out. The diaphragm might not be seen directly in CT and MRI images. It consists of muscular and ligamentous parts. The muscular (elastic) parts of the diaphragm are fixed to anatomical structures, which can be segmented from CT and MRI images (ribs, vertebra, and pericardium). The ligamentous (inelastic) parts can be found at the bottom of the lung forming the border between lung and abdominal cavity. A first order approximation to the estimation of the lower long surface is thus to take into account the elastic parts of the diaphragm during breathing and to calculate its shape based on the surface coordinates, such as the measured outer shape and the estimated external abdominal volume.

Tumor Position Estimation

Once the organ, such as lung, surface is estimated based on the measurement of the outer shape of the patient's body, the boundary conditions for a biomechanical model of the lung including the tumor are known. In a first order approximation, the lung tissue can be modeled as a spongy tissue in which an incompressible (or even rigid) tumor is embedded. FEM methods can be used to predict the tumor position based on this model.

In another embodiment there is provided a method wherein the biomechanical model comprises a patient-specific mesh of chest, the organ and abdomen. In a particular embodiment, there is provided:

1. A patient-specific mesh of chest, lung, and abdomen. This mesh can be created from preoperative CT scans that are routinely acquired.

2. Surface coordinates, such as displacement surrogate signals (a combination of):
   a. Motion of the chest
   b. Motion of the umbilicus
   c. Motion of several skin markers on the abdomen
   d. Volume of the abdomen These parameters can be measured using optical shape sensing or other tracking methods such as optical or electromagnetic trackers.

3. A model-based approach to calculate the motion of the diaphragm from the surrogate signals.

4. An FE-based algorithm to compute the motion of the lung from the diaphragm motion.

The model could be divided into two parts:

The first part calculates the motion of diaphragm from the surrogate signal, measured in the abdominal region.

The second part calculates the lung motion from the calculated diaphragm motion in part 1 and chest motion surrogate signal.

In order to calculate the diaphragm motion form the surrogate signal a learning approach may be employed. In this method the diaphragm motion pattern is learned from a set of clinical data. There are several methods available to learn the diaphragm motion pattern. In one embodiment, principal component analysis can be used. In this method, the diaphragm motion of a group of patient is transferred into its principal components. A few components with the highest corresponding singular value can be selected as representatives of the diaphragm motion pattern. Other embodiments can include model fitting approaches or neural networks. Then the patient specific model is solved in a way that the calculated diaphragm motion has a similar pattern to the learnt pattern.

In one embodiment an FE-based model can be used to calculate the diaphragm motion from the surrogate signal. In this case, the displacement vector u is confined to have the same pattern as the learnt displacement vector (a weighted summation of principal components). Moreover, the known displacements from the surrogate signals can be exchanged with unknown forces in equation (1) so that equation is sufficiently constrained to be solved. Note that most of entries in f are zero as there is no external force. In this case, the diaphragm motion can be calculated without a need to measure forces or pressures or use an inaccurate predefined value.

The second part of the algorithm uses the calculated diaphragm motion from the first part. We assume that the lower portion of the lung is attached to the diaphragm and moves with it. Therefore, in equation (1) some of the displacement will be known that can be exchanged for corresponding unknown forces. The same can be said about the chest wall motion if measured. Therefore, the lung motion can be calculated without incorporation of force or pressure values.

Figure 8:
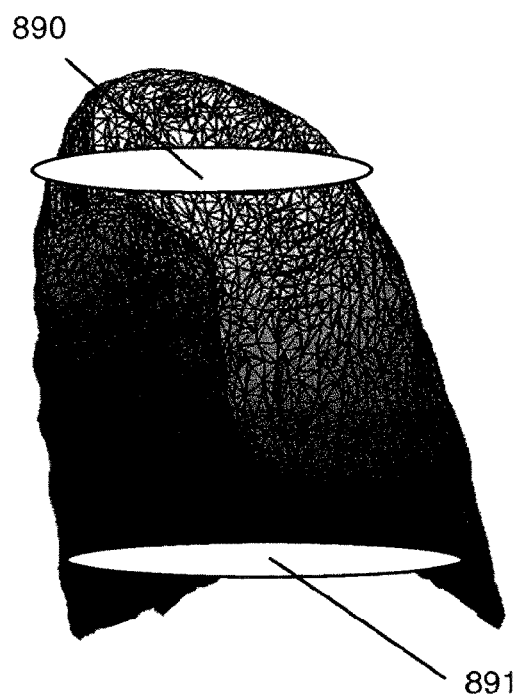
FIGS. 8-9 illustrate examples of a lung finite element mesh and applied displacement boundary conditions.
Figure 9:
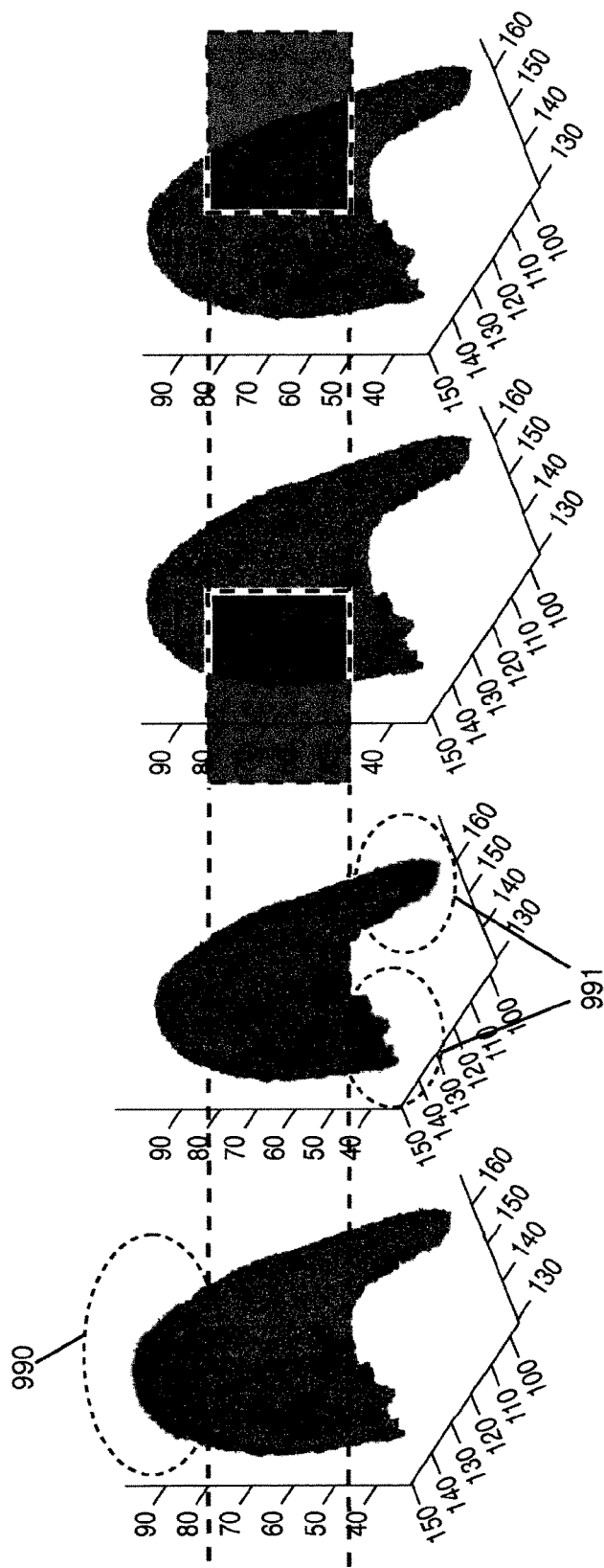

FIGS. 8-9 illustrate examples of a lung finite element mesh and applied displacement boundary conditions. More specifically, FIGS. 8-9 show two examples of the lung finite element mesh and applied displacement boundary conditions.

FIG. 8 shows top nodes 890 being fixed to the chest bones, bottom nodes 891 move with the diaphragm and the side nodes are free.

FIG. 9 shows top nodes 990 and side nodes are fixed to the chest bones, bottom nodes 991 move with the diaphragm and the side nodes are free.

Figure 7:
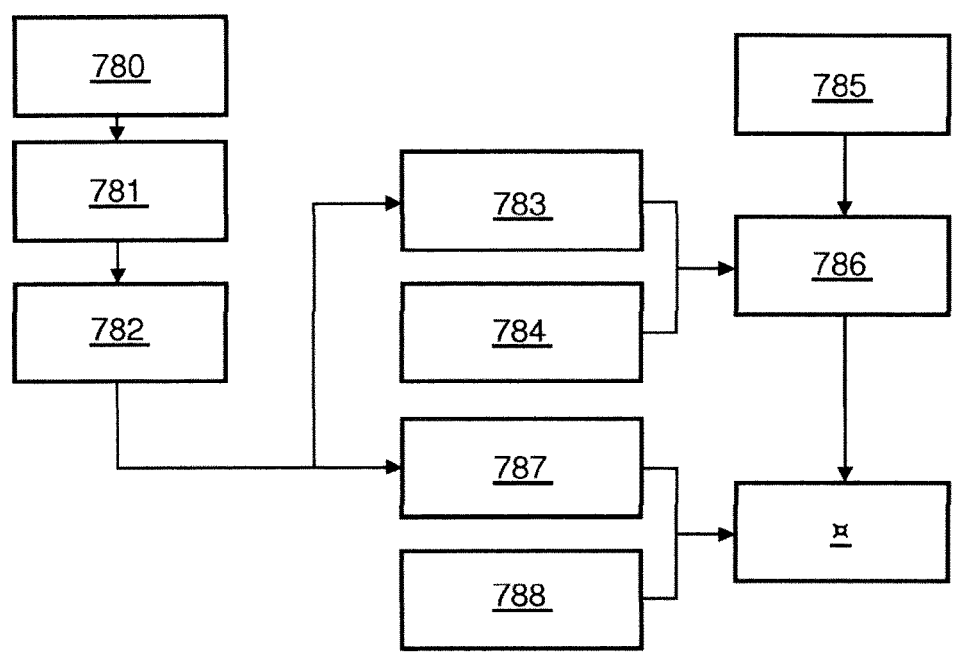
FIG. 7 is a flow chart illustrating a method according to an embodiment of the invention.

FIG. 7 is a flow chart illustrating a method according to an embodiment of the invention where the organ is a lung, wherein three-dimensional data is acquired 780, such as acquired with CT scanning (similar to the patient being imaged by an imaging unit 325 for obtaining 3D data 342 indicative of positions of internal structures, which imaging unit may be a CT-scanner or an NMR scanner in FIG. 3), the three-dimensional data is segmented 781 into lung, chest and abdomen (similar to the 3D data 342 being received by an image segmentation unit 344, which may provide information regarding lung surface 346, diaphragm surface 348, and abdomen surface 350 during the first imaging phase in FIG. 3), a patient specific mesh is generated 782, a finite element model 783 of the abdomen is generated, learnt constraints, the finite element model 783 of the abdomen and surface coordinates 785 are employed to calculate 786 diaphragm motion, a finite element model 787 of the chest and lung is generated, the finite element model 787 of the chest and lung, surface coordinates 788 indicative of a position and shape of at least a part of the surface of the thorax (356) of said associated patient, and the diaphragm motion 786 are employed to calculate lung motion.

In addition to or as an alternative to the CT datasets, other imaging datasets such as MRI, Ultrasound, X-ray, PET-SPECT, flow etc. may be used. During therapy, the breathing pattern and cycle can also be identified.

To achieve a patient-specific model from a generic database of the population, specific features can be extracted. One example of the same would be the shape of the diaphragm, wherein a person having a flat diaphragm could match better with those in the database that have a similar shape. Another example is the size of the diaphragm which may also be correlated with the patient's size and weight.

In order to accurately predict lung and tumor motion, the motion at certain points like the umbilicus or sternum may be computed and transformed to the abdominal volume. To accommodate for variations in breathing patterns, each pattern could be sorted into a multi-dimensional phase space.

It is understood by one skilled in the art that any patient or volunteer database may comprise datasets that are normalized, in order to account for inter-trial variations.

To sum up, the invention provides a method and apparatus to measure the surface of the patient (thorax and abdominal regions), e.g., during therapy delivery and (optionally, such as if necessary) while imaging. Together with biomechanical considerations the position of internal structures of the patient, such as an organ, and optionally a tumor in an organ, is inferred from the measured patient surface. In case the patient breathes and thus the organ and/or tumor moves, the position may be determined, which may be advantageous during, e.g., radiation therapy, since it enables that whenever the tumor is at the right position according to the radiation therapy plan, the radiation is switched on. In a specific embodiment, a finite element model is employed.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for estimating organ coordinates of at least a part of an organ which may move and/or change shape due to breathing in an associated patient, the method comprising:

using a processor, obtaining a biomechanical model of said associated patient, said biomechanical model being based on three-dimensional data indicative of only internal structures of a thorax of said associated patient at a first point in time;

using a surface determining unit comprising a surface scanner, a fiber optic shape sensing (OSS) garment, or a plurality of cameras, obtaining surface coordinates indicative of a position and shape at a second point in time of at least a part of the surface of the thorax of said associated patient and at least a part of the surface of the abdomen of said associated patient so as to enable estimating an external abdominal volume; and using the processor, obtaining the organ coordinates; including at least organ coordinates of a diaphragm by inputting said surface coordinates in said biomechanical model and outputting from said biomechanical model the organ coordinates, wherein said biomechanical model models at least a part of an internal abdominal volume, and tissue of the chest wall of said patient, as incompressible.

2. A method according to claim 1, wherein said biomechanical model employs as constraints, at least a part of the internal abdominal volume, and the surface coordinates indicative of a position and shape of at least a part of the surface of the thorax of said associated patient.

3. A method according to claim 1, wherein said biomechanical model is based on three-dimensional data indicative of only internal structures of the thorax of said associated patient obtained by a single 3D scan.

4. A method according to claim 1, wherein the surface coordinates serve as the exclusive input to the biomechanical model in the step of obtaining organ coordinates at a second point in time.

5. A method according to claim 1, wherein said organ is a lung including the lower boundary comprising the diaphragm.

6. A method according to claim 1, wherein the method further comprising determining a tumor coordinate indicative of a position of a tumor in the organ, wherein the determination is based on the organ coordinates.

7. A method according to claim 6, wherein the method further comprising repeatedly determining a tumor coordinate indicative of a position of a tumor in the organ, wherein the determination is based on the organ coordinates.

8. A method according to claim 6, wherein the biomechanical model comprises a patient-specific mesh of chest, the organ and abdomen.

9. A method according to claim 6, wherein the method further comprising any one of:

outputting the tumor coordinate, so as to enable an associated device to receive the tumor coordinate, outputting a signal indicative of whether or not the tumor coordinate is within a pre-determined volume.

10. An apparatus for estimating coordinates of at least a part of an organ which may move due to breathing in an associated patient, the apparatus comprising:

a non-transitory computer-readable medium suitable for comprising a biomechanical model of said associated patient, said biomechanical model being based on three-dimensional data indicative of internal structures of a thorax of said associated patient and a portion of an abdomen of said patient at a first point in time, a surface determining unit for obtaining surface coordinates indicative of a position and shape at a second point in time of at least a part of the surface of the thorax of said associated patient, and at least a part of the surface of the abdomen of said associated patient so as to enable estimating an external abdominal volume, a processor operatively connected to the computer readable medium and the surface determining unit for obtaining surface coordinates indicative of a position and shape of the surface of said associated patient at the second point in time, the processor being arranged for obtaining the organ coordinates, by receiving said surface coordinates, inputting said surface coordinates in said biomechanical model, and outputting from said biomechanical model the organ coordinates, wherein said biomechanical model is configured to models at least a part of an internal abdominal volume, and tissue of the chest wall, as incompressible.

11. An apparatus according to claim 10, wherein the surface determining unit for obtaining surface coordinates indicative of a position and shape of the surface of said associated patient, comprises any one of:

a surface scanner, a fiber optic shape sensing (OSS) garment, and/or a plurality of cameras enabling photogrammetry.

12. An apparatus according to claim 10, further comprising a source of radiation for external beam therapy which is operatively connected to the processor.

13. An apparatus according to claim 12, wherein the source of radiation for external beam therapy is arranged for functioning dependent on the position of tumor.

14. An apparatus according to claim 10, wherein the computer-readable medium comprises the biomechanical model of said associated patient.

15. A non-transitory computer readable medium having a computer program stored thereon, the computer program enabling a processor to carry out the method of claim 1.

16. The apparatus according to claim 10, wherein the processor is further programmed to:

determine a tumor coordinate indicative of a position of a tumor in the organ, wherein the determination is based on the organ coordinates.

17. An apparatus, comprising:

a database storing a biomechanical model of an associated patient, the biomechanical model being based on three-dimensional data indicative of internal structures of at least a thorax of said associated patient at a first point in time;

a surface determining unit comprising a surface scanner, a fiber optic shape sensing (OSS) garment, or a plurality of cameras configured to obtain surface coordinates indicative of a position and shape at a second point in time of at least a part of the surface of the thorax of said associated patient and at least a part of the surface of the abdomen of said associated patient so as to enable estimating an external abdominal volume;

a processor operatively connected to the database and imaging device, the processor being programmed to:

retrieve said biomechanical model from the database;

receive said surface coordinates from the imaging device;

input said surface coordinates into said biomechanical model; and output from said biomechanical model organ coordinates including at least organ coordinates of a diaphragm, wherein said biomechanical model is configured to model at least a part of an internal abdominal volume, and tissue of the chest wall, as incompressible.

18. The apparatus according to claim 17, wherein the processor is further programmed to:

determine a tumor coordinate indicative of a position of a tumor in the organ from the organ coordinates.

19. The apparatus according to claim 18, further comprising:

a radiation therapy source configured to deliver therapy to the associated patient;

wherein the processor is configured to control operation of the radiation therapy source to delivery therapy to the determined position of the tumor.

20. The apparatus according to claim 17, wherein the processor is programmed to input only said surface coordinates into said biomechanical model whereby the biomechanical model outputs the organ coordinates including at least organ coordinates of the diaphragm using only said surface coordinates.

* * * * *